Figure 3:
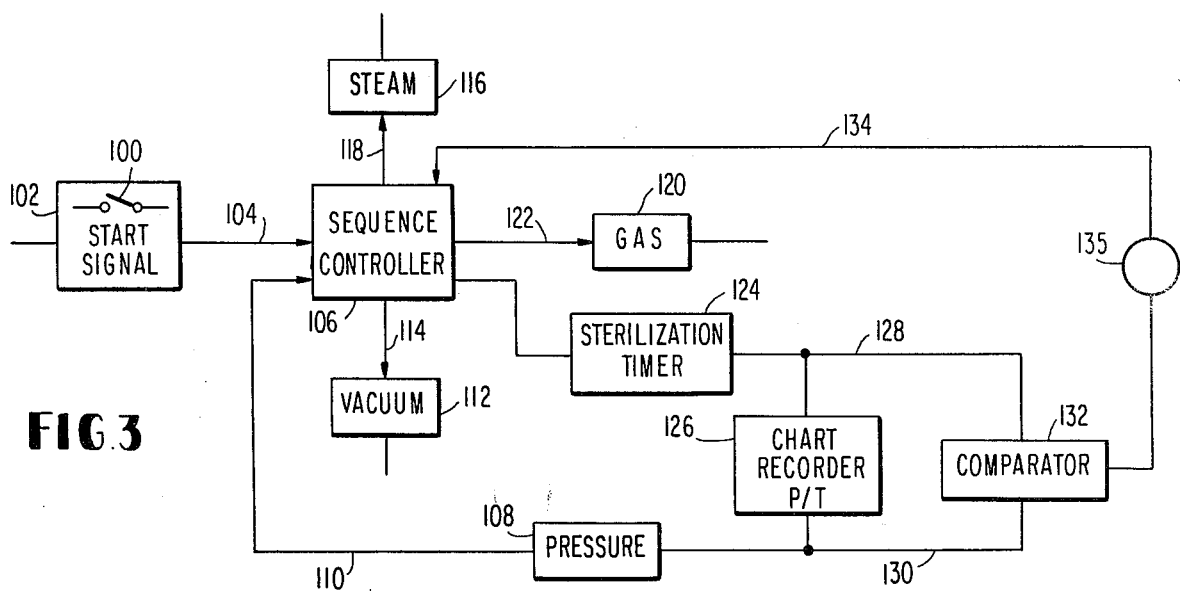

United States Patent [19]

Young

[11] Patent Number: 4,457,892
[45] Date of Patent: Jul. 3, 1984

[54] BIOCIDAL GAS STERILIZATION AND GAS LEAKAGE DETERMINATION

[75] Inventor: Jack H. Young, Cambridge Springs, Pa.

[73] Assignee: American Sterilizer Company, Erie, Pa.

[21] Appl. No.: 9,817

[22] Filed: Feb. 6, 1979

[51] Int. Cl.³ .............................................. A61L 2/20
[52] U.S. Cl. ......................................... 422/2; 422/3; 422/33; 422/34; 422/117
[58] Field of Search .................... 422/34, 27, 2, 3, 33, 422/37, 28, 26, 112, 114, 116, 117, 295, 300; 23/230 L

[56] References Cited

U.S. PATENT DOCUMENTS

| | | | |
|---|---|---|---|
| 2,080,179 | 5/1937 | Merriam et al. | 422/27 |
| 2,131,134 | 9/1938 | Baer et al. | 422/31 |
| 2,188,371 | 1/1940 | Merriam | 131/133 |
| 3,035,886 | 5/1962 | Hickey | 422/27 |
| 3,068,064 | 12/1962 | McDonald | 422/34 |
| 3,206,275 | 9/1965 | Sair et al. | 422/33 |
| 3,372,980 | 3/1968 | Satas | 422/34 X |
| 3,549,312 | 12/1970 | Ernst | 422/34 X |
| 3,598,516 | 8/1971 | Shull et al. | 422/27 |
| 3,795,483 | 3/1974 | Grafingholt | 422/26 X |
| 3,861,875 | 1/1975 | Joslyn | 422/111 X |
| 3,910,761 | 10/1975 | Hopkins | 422/108 |
| 3,954,406 | 5/1976 | Chamberlain | 422/27 |
| 3,981,701 | 9/1976 | Anderson et al. | 23/230 L X |
| 4,130,393 | 12/1978 | Fox | 422/34 X |

FOREIGN PATENT DOCUMENTS 3137 of 1903 United Kingdom .
488638 7/1938 United Kingdom .

OTHER PUBLICATIONS

"Developments in Industrial Microbiology"; vol. 18,; Soc. for Industrial Microbiology; pp. 335-351.
J. J. Perkins; "Principles & Methods of Sterilization in Health Sciences"; Pbl. by C. C. Thomas; Springville, Ill, pp. 520-527.

Primary Examiner—Barry S. Richman
Attorney, Agent, or Firm—Shanley and Baker

[57] ABSTRACT

Methods and apparatus for the timely determination of potentially harmful biocidal gas leakage from a pressurized chamber during sterilizing operations are disclosed. Biocidal gas make-up values are monitored during the sterilizing phase to provide prompt warning of biocidal gas leakage. In one embodiment, the timing of preselected pressure increment gas make-up charges are measured and compared to minimum acceptable gas make-up charge times. In addition, absorption of biocidal gas by the load can be compensated for in sterilizing operations where load absorption is a significant factor. Also, provision is made for predicting gas absorption by the load from steam absorption data obtained during pressure-controlled conditioning cycles.

9 Claims, 4 Drawing Figures

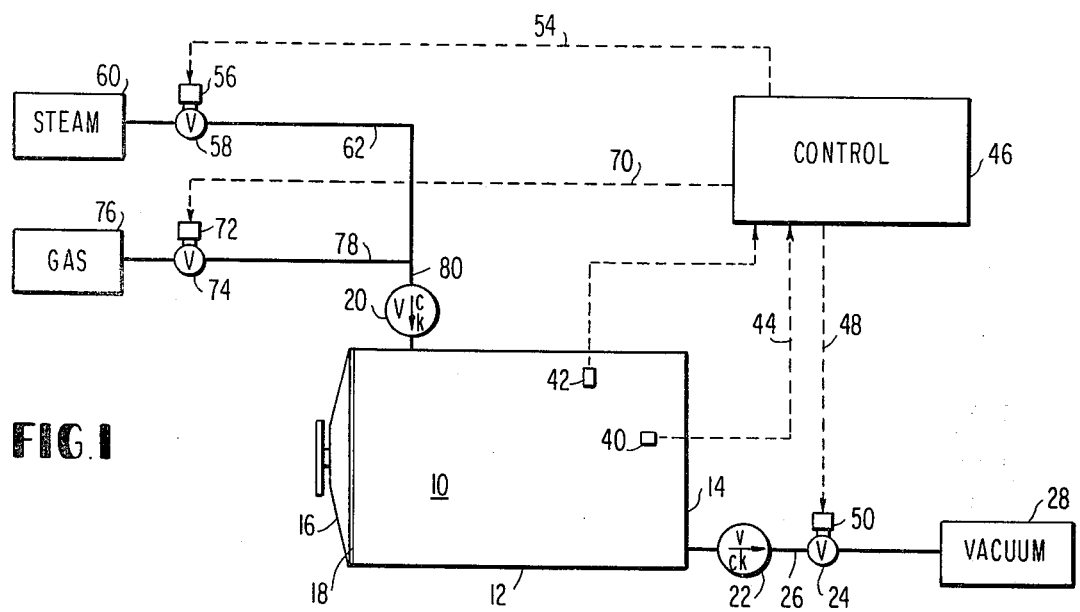

BIOCIDAL GAS STERILIZATION AND GAS LEAKAGE DETERMINATION

This invention is concerned with biocidal gas sterilizing and, more particularly, with the novel concept of, and sterilizing methods and apparatus for providing, timely determination of potentially harmful biocidal gas leakage during gas sterilization.

Chemical gases used in sterilizing such as ethylene oxide, methol bromide, and similar alkylating agents produce a protein denaturization in microorganisms. Ethylene oxide (ETO) is widely used in hospital and industrial gas sterilizers. Known biological hazards of ETO exposure to humans include eye and skin irritation; also, there have been prognostications of carcinogenic properties. As a result, strict regulations on the use of such biocidal gases have been promulgated by governmental regulatory bodies and safety measures have been receiving increasing emphasis.

Measures have been advanced for safe discharge of ETO after a sterilizing cycle to reduce operator exposure. However, neither the concept nor measures have been advanced for determining potentially harmful ETO leakage from a sterilizer during sterilizing operations; nor have means been provided for early warning and terminating such leakage which might otherwise go undetected.

A primary object of the present invention is an early determination of unacceptable biocidal gas leakage from a sterilizing chamber during a sterilizing cycle. Pressure vessels to be used as sterilizing chambers are manufactured to prescribed tolerances, e.g. about two (2) mm Hg. per minute leakage rate, and tested before being put into use in biocidal gas sterilizing operations. During usage, sterilizing chambers are sealed for operating at pressure other than atmospheric. The largest sealing site surrounds the sterilizing chamber door which provides access for loading the chamber with goods to be sterilized. Such closures are sealed by compression of gasket material; or, often, such gasket material is pneumatically inflated or pneumatically moved into sealing relationship with a closure sealing surface on the sterilizer. Such gasket materials are subject to wear and fatigue with usage and become one of the most prevalent sources of harmful leakage. Other causes of gas leakage into the environment of the sterilizer can include check valves, compression tubing fittings, and other valving arrangements on supply and exhaust piping to the chamber shell where such valving arrangements help define the chamber volume subject to biocidal gas pressure.

Wear or fatigue problems associated with gasket materials may not be discernible during load conditioning phases which are generally carried out when the chamber is in an evacuated state. Vacuum conditions within a chamber generally aid sealing of worn or faulty gasket material so that a determination of harmful leakage of biocidal gas, to be timely and meaningful should, in accordance with the present teachings, be available when the chamber is under biocidal gas pressure. And, the determination should be available early after establishment of biocidal gas pressure and, also, throughout the sterilizing phase.

The concept of a timely determination of biocidal gas leakage is a significant contribution of the invention; other advantages and contributions are considered in a more detailed description of the inventive methods and apparatus presented with reference to the accompanying drawings.

Figure 4:
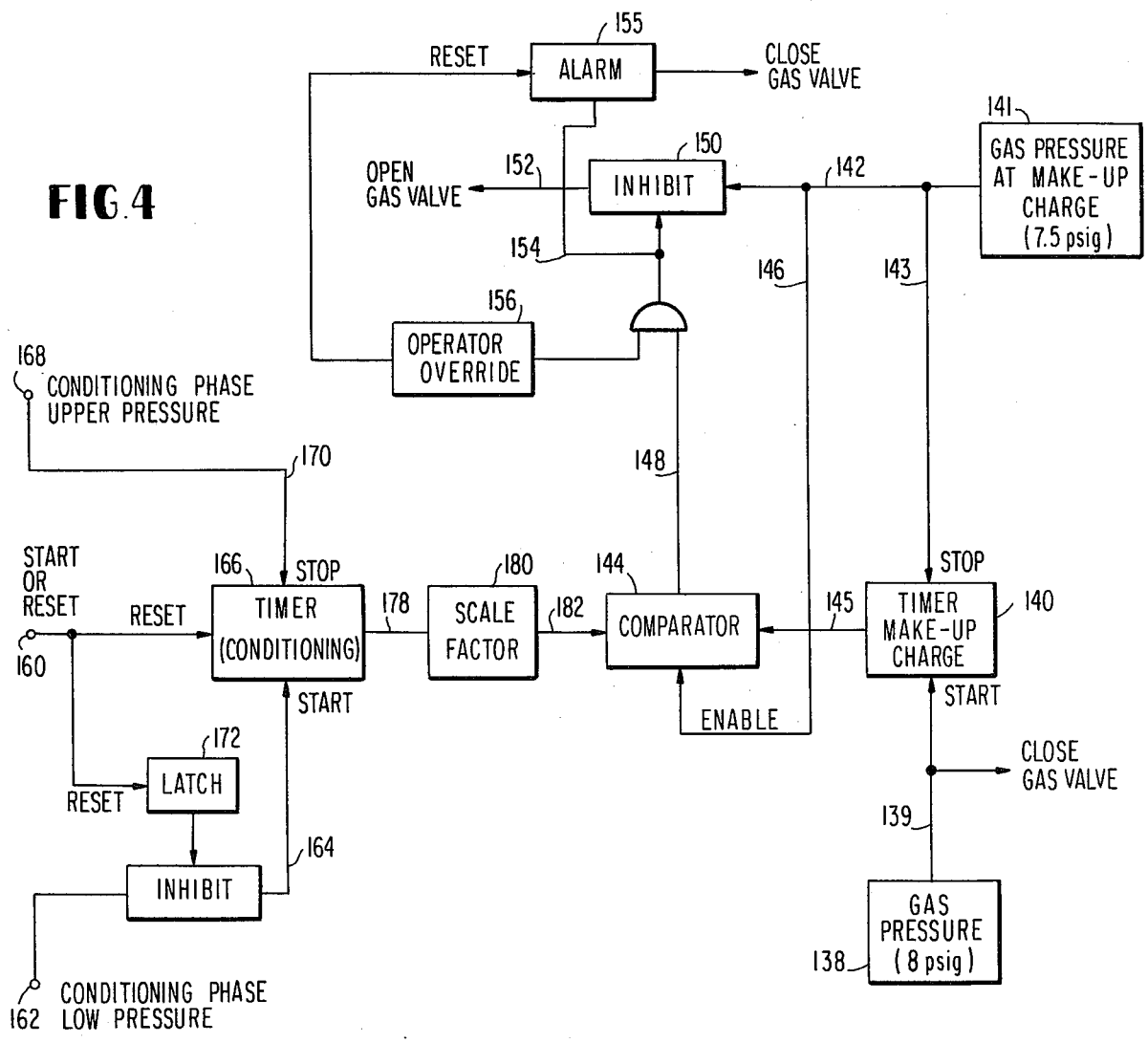

In these drawings:

FIG. 1 is a schematic representation of gas sterilizing apparatus embodying the invention, FIG. 2 is a graphical pressure vs. time presentation of a gas sterilizing cycle embodying the invention, FIG. 3 is a diagrammatic illustration of apparatus embodying the invention, and FIG. 4 is a control apparatus schematic for carrying out the invention.

Referring to FIG. 1, a chamber 10 is defined by side wall 12, rear wall 14, and access door 16. After loading the chamber with goods to be sterilized, the door 16 is closed and sealed for operation at pressures other than atmospheric. Gasket 18 provides for sealing of the door where contact is made with the chamber shell. The volume subject to pressures other than atmospheric can include portions of conduits leading to and from the chamber dependent on piping and various locations for check valves 20 and 22.

After loading and sealing, chamber 10 is generally subjected to an initial evacuation by opening valve 24 in conduit 26 connecting vacuum source 28 to the chamber 10.

This initial evacuation, as shown in FIG. 2, can extend from atmospheric pressure level at point 30 to approximately sixty (60) mm Hg. at point 32. After the initial evacuation, a conditioning vapor such as steam is added to heat and moisturize the load. Conditioning of the load can include repressurization as indicated by line 34 of FIG. 2, between a lower subatmospheric pressure at point 32 and an upper subatmospheric pressure at point 36. The initial evacuation along evacuation line 31 of FIG. 2 and repressurization along line 34 can be controlled with pressure switches forming part of pressure sensor means 40 of FIG. 1.

In place of a pressure sensor, other sensing means can be used in sterilizing cycles in which the load is conditioned by other methods. For example, sensor 42 can comprise a relative humidity gage which will control conditioning steam addition to hold chamber relative humidity at a desired level; or, in other commercially known conditioning phases, sensor 42 can be temperature sensitive and located near the drain line to control steam flow through the chamber to heat the load by steam flow.

In sterilizing cycles utilizing pressure sensing for control of conditioning the goods to be sterilized, pressure signals over line 44 to control 46 provide proper sequencing; e.g. a signal over line 48 to solenoid 50 (FIG. 1) terminates initial evacuation when a desired subatmospheric pressure, such as sixty (60) mm Hg., is reached at point 32 (FIG. 2). Upon closing of evacuation valve 24, a signal from control 46 on line 54 to solenoid 56 opens steam valve 58. Steam from source 60 flows through conduit 62 into chamber 10 and raises the pressure within the chamber as indicated by repressurization line 34. Cyclic evacuation and steam injection can be carried out during the conditioning phase of the sterilizing cycle between point 36 and point 64 to raise the temperature and moisten the goods to be sterilized to desired levels.

Upon completion of the conditioning phase, a biocidal gas is charged along gas pressurization line 66 (FIG. 2) from a subatmospheric level at point 64 to a pressure above atmospheric level at point 68.

Referring to FIG. 1, biocidal gas charge can be controlled by a high pressure switch forming part of pressure sensing means 40 which sends a signal along line 44 to control 46. From control 46, a signal in line 70 to solenoid 72 controls valve 74 which permits biocidal gas to flow from source 76 through conduit 78 to conduit 80 and through check valve 20 into chamber 10. Evacuation valve 24 is closed during such gas charge and during the sterilizing phase of the cycle between points 68 and 82 of the cycle graph of FIG. 2.

As is known, sterilization with ETO is based on an integrated effect of load temperature and moisture, ETO concentration, and time. With load temperature at about 130° F., the load moisturized to between about 40% to 100% relative humidity, and a gas concentration of about 650 mg/l of sterilizer volume, sterilization with an adequate safety factor can be carried out in less than two hours. At lower temperatures, sterilization time is increased and at higher temperatures sterilization time is decreased.

Typically a biocidal gas comprising ETO includes about 12% ETO and about 88% of a diluent such as freon. With this gas mixture, after conditioning which includes evacuation to about the level shown in FIG. 2, a chamber pressure of about 8 psig provides an ETO concentration of about 650 mg/l. Other pressure levels can be selected for varying concentrations or other ETO mixtures. In ordinary practice, a gas pressure from above five (5) psig to about fifteen (15) psig, and higher, would be used.

In order to maintain desired ETO concentration, the pressure selected, e.g. eight (8) psig, is maintained during the sterilization phase by controlling gas valve 74 through control 46. If a preselected pressure increment drop (e.g. about one-half pound of pressure) occurs, a make-up charge of biocidal gas is introduced during the sterilizing phase to hold desired pressure level and, in turn, ETO concentration. Within prescribed tolerances, a make-up charge based on an incremental pressure drop of about one-half pound should not occur in less than a prescribed interval of about fifteen minutes. In accordance with the invention, the make-up charge values for biocidal gas are monitored to determine whether an unacceptable ETO leakage rate exists. By monitoring make-up charging, a call for supplemental ETO in less than a prescribed interval, e.g. fifteen minutes, indicates unacceptable gas loss. Also, the slope of the pressure curve 92 can be compared to the accepted slope (pressure decrease vs. time) value in quantitatively monitoring make-up charging rate of biocidal gas to determine gas leakage.

With some sterilizers, load absorption of gas is compensated for to facilitate early and accurate determination of ETO leakage. The duration of gas charge along line 66 of FIG. 2 is dependent on the flow rate of ETO and chamber size; gas charge can take from a few minutes to fifteen minutes, or more. After reaching desired biocidal gas pressure at point 68 and interrupting gas charge, an initial make-up charge of biocidal gas may be called for in a short interval due to absorption of the biocidal gas by the goods to be sterilized. When applicable, such a load-absorption decrease in chamber pressure along line 84 will be dependent upon such factors as load characteristics and volumetric relationship of the load, chamber, and gas charge. A soft goods load, e.g. fabric or rubber goods, exhibits maximum absorption characteristics while a hard goods load, such as metal surgical instruments, exhibits minimal absorption characteristics. Most full loads are mixed soft goods and hard goods since hard goods are often wrapped in muslin. Where ETO absorption is a factor, pressure decreases along line 84 until some incremental pressure level is reached at point 86 which, through control 46, calls for a make-up charge of gas along line 88 (FIG. 2) returning chamber pressure to a selected level, such as 8 psig, at point 90.

In accordance with the invention, parameters for such a load-absorption repressurization with ETO biocidal gas can be pre-established or calculated. In practice, compensating for load absorption can have more relevance and significance when working with large volume industrial sterilizers than the smaller hospital units. In the operation of most hospital sterilizers, a major portion of initial load absorption can take place during the gas charge. Where load absorption after gas charge is significant for a particular sterilizer, the load absorption charge required can be ascertained empirically for differing loads and the time and pressure increment values for an average load established. The initial load absorption can be compensated for directly with these values or the slope of the load-absorption curve can be established and utilized in analyzing make-up charging rate.

Measuring the timing of each make-up charge, succeeding any load absorption compensation, or starting at point 68 when load absorption is not a significant factor, provides an early evaluation of ETO leakage. A time value along the horizontal component of line 92 and, a pressure increment along line 94 are established for a make-up charge within accepted tolerances; e.g. a half pound make-up in a time interval of fifteen minutes, or more, could be considered within accepted tolerances for a particular sterilizer.

Where load absorption is not a significant factor for a particular sterilizing operation, the time of line 92 would be started at point 68 to provide early determination of harmful biocidal gas leakage. If a make-up charge is called for in any lesser time than the accepted interval, e.g. at point 95 of FIG. 2, this determines that an unacceptable ETO leak rate exists and, addition of biocidal gas is interrupted. Also, the sterilizing phase can be terminated and sterilizing gas exhausted from the chamber based on such determination of an unacceptable ETO leakage rate, or, the entire cycle can be aborted.

The parameters for acceptable make-up charges are utilized while the chamber is under gas pressure and a continuing evaluation made throughout the sterilization phase. An incremental make-up charge as indicated by line 96, when called for in less than the preset interval as indicated by line 97, would therefore automatically determine unacceptable leakage at any time and initiate procedures for termination. A visual or audible warning would preferably be part of any determination of ETO leakage.

Load absorption characteristics can be evaluated and predicted more readily with conditioning methods which exhibit a repressurization curve, as represented by line 34 of FIG. 2. A functional relationship exists between the time required for conditioning vapor pulsing phases and the percentage of soft goods in the load which provides an indication of load characteristics.

In brief, referring to FIG. 2, if steam repressurization at a predetermined steam injection rate occurs along a steep line, approaching vertical, i.e. in a very short time interval, a predominantly hard goods load is indicated.

As the slope of line 34 takes on more of a horizontal component, i.e. a longer time interval between points 32 and 36, a load with a greater percentage of soft goods is indicated. Gradient points between a full hard goods load and a full soft goods load can be readily established empirically. The interrelationship for any load can be extrapolated graphically or computed. Such data held in a memory unit forming part of a comparator means can be used for predicting ETO absorption characteristics of a load.

While steam absorption by a load has a different time factor than ETO absorption, due to inherently higher penetrability properties of ETO, the absorption times for each can be interrelated with a proportionality factor which can be readily scaled. Conversion from steam absorption data to gas absorption data can be readily made electronically by introducing the sequence scale factor for shifting from one set of data to another.

It should be noted that this functional relationship remains reliable, for practical purposes, whether dealing with partial loads consisting of soft goods or full loads which are partially soft goods; i.e. an indication of 50% fabric load would be approximately the same whether the soft goods 50% of load capacity was in a full or partial load.

When establishing the functional relationship using ETO, gradient points of ETO absorption, i.e. decrease in chamber pressure from a preselected pressure during a fixed time interval, can be established empirically utilizing differing percentages of load capacity as soft goods; intermediate points can be extrapolated graphically or computed. These data can be stored in a computer memory or other comparator means. Such functional relationship data between steam and ETO provides a proportionality factor which enables a steam conditioning phase, e.g. line 34 of FIG. 2, to be readily used to predict what the slope of ETO absorption line 84 should be.

In brief, the load characteristic evaluation available during conditioning can be used to predict biocidal gas load absorption and what the slope load absorption line 84 should be in sterilizers where load absorption is a significant factor. With such data, an earlier or preliminary indication of unacceptable ETO gas leakage can be made based on the predicted slope of line 84. Such preliminary indication can be accomplished when a make-up charge is called for in a shorter time interval than that predicted based on load characteristics or by analyzing the slope of the pressure decrease line 84; a steeper slope than predicted would indicate unacceptable leakage. The steps upon this determination can be as previously enumerated, i.e. stopping gas charge, providing a visual or audible warning, and/or exhausting the chamber of sterilizing gas and/or aborting the entire cycle.

When any of the above embodiments for making an evaluation early in the sterilization phase do not indicate an unacceptable leakage rate, the sterilization phase can proceed along line 98 to complete desired sterilization; and, then, to exhaust the chamber as represented by exhaust line 99. Monitoring gas make-up continues, however, throughout the sterilization to determine if any leaks occur at any part of that phase.

Referring to FIG. 1, individual elements of the apparatus such as solenoid controlled valves, steam, gas and vacuum sources, check valves, sterilizing chamber and seals, pressure sensing means and cycle control means for various gas sterilization cycles are so well known that no additional description is needed. Monitoring gas make-up charging rate with comparison to a standard to determine potentially harmful ETO gas leakage also utilizes electromechanical or electronic elements which are individually known but, in a new combination. The overall control arrangement including conditioning phase, sterilization phase, and ETO leakage indication is shown diagramatically in FIG. 3.

Referring to FIG. 3, with start-up at switch 100, signal generator 102 delivers a signal along line 104 to sequence controller 106. In a sterilizing cycle such as that shown in FIG. 2, the conditioning phase can be pressure responsive. Pressure sensing means 108 direct signals over line 110 to the sequence controller 106. The chamber is exposed to vacuum 112 through signal line 114 and steam is injected from source 116 through signal line 118. The pressure sensing means 108 can include pressure switches responsive to subatmospheric chamber pressures encountered during conditioning; for example, at 60 mm Hg., to stop evacuating and start steam injection; then, at 90 mm Hg., to stop steam injection and start evacuation. Such pressure responsive pulsing continues until desired conditioning is completed. Then, sequence controller 106 initiates gas charge from source 120 by a signal on line 122.

When a predetermined biocidal gas pressure has been reached, sterilization phase timer 124 provides for holding biocidal gas pressure for the selected sterilization time responsive to pressure sensor means 108. Chamber gas pressure can be recorded vs. time on recorder chart 126 responsive to signals on lines 128 and 130 while the desired chamber gas pressure is held via pressure signals to sequence controller 106 for the selected sterilization time.

Make-up charges of biocidal gas are compared to predetermined parameters of pressure increment and time, as previously described, in comparator 132. A determination of ETO leakage generates a signal on line 134 to warning indicator 135 and to sequence controller 106 to interrupt gas injection and/or abort the cycle and exhaust the chamber.

Also, when utilizing load characteristic evaluation, a predicted ETO absorption rate can be compared to the actual gas absorption make-up charge curve 84 in comparator 132.

FIG. 4 shows a circuit schematic for monitoring gas make-up charging rate and carrying out control electronically. In an embodiment in which time and pressure increment values for an acceptable gas make-up charging rate are established, e.g. about ½ pound in fifteen or more minutes, a determination of ETO leakage is made responsive to a make-up requirement occurring in less than the established time interval, only a portion of the apparatus combination shown schematically in FIG. 4 is utilized. For example, when a selected gas pressure, such as eight (8) psig is established, pressure sensing means 138 with a signal on line 139 interrupts gas charge and starts timer 140 which is preset for the established time interval, e.g. fifteen minutes. When pressure sensing means 141 indicates a make-up should be made, a signal is sent over line 142 and over line 143 to timer 140 which, in turn, sends a signal to comparator 144 over line 145. The comparator 144 is activated by a signal over line 146. When the timed interval is greater than the pre-established value, no signal is sent on line 148 to activate inhibit means 150 and the signal on line 142 causes a signal on line 152 to open the gas valve for acceptable gas make-up. When the time interval for a make-up charge is less than that pre-established, a signal from comparator 144 to inhibit means 150 prevents opening of the gas valve and a signal on line 154 activates a visible or audible alarm 155 and can initiate the other termination procedures described above. An operator override at 156 can permit operator evaluation before initiating cycle termination procedures.

When it is desired to use load absorption evaluation, conditioning phase values can be used to predict expected gas absorption. For example, the repressurization time between a lower and upper subatmospheric pressure during conditioning, as previously described, can be used to indicate steam absorption characteristics. A signal at input terminal 160 starts, or resets, the control. A conditioning phase low pressure (e.g. 60 torr.) signal is delivered to input terminal 162 and, unless inhibited, sends a signal over line 164 to timer 166. The conditioning phase upper pressure (e.g. 90 torr.) value is introduced at input terminal 168 and delivered to timer 166 on line 170. Latch 172 inhibits initiation of the timer 166 until the proper steam pulsing time in the conditioning phase, e.g. inhibiting signals during the initial evacuation of the chamber.

The conditioning phase time on line 178, through scale factor means 180, which translates steam absorption values to gas absorption values, delivers a signal to comparator 144 on line 182 indicating when a gas absorption make-up charge is to be expected. Earlier described make-up charging apparatus, through timer 140, sends a signal representative of the actual make-up charge time. Comparator 144 functions as described earlier; if a make-up charge is called for in a shorter time interval than predicted, an unacceptable leakage is indicated and evaluation or termination procedures are undertaken.

By use of proper scale factor values, the slope of the predicted gas absorption curve can be compared to that of the actual gas absorption curve to make a determination along line 84 whether unacceptable ETO leakage is occurring.

While specific embodiments with specific values for carrying out the invention have been set forth, it should be understood that various modifications can be made in these specifics while utilizing basic principles and contributions of the invention. Therefore, in analyzing the scope of the present invention, reference should be had to the accompanying claims.

We claim:

1. Gas sterilization process utilizing a chemically biocidal gas and providing leakage determination of such biocidal gas from a sterilizing chamber comprising, after loading the sterilizing chamber with goods to be sterilized and sealing such chamber for operation at pressures other than atmospheric, the steps of
    charging chemically biocidal gas into the sterilizing chamber,
    establishing a desired concentration of such biocidal gas within the sterilizing chamber,
    providing a sterilization phase at a pressure above atmospheric to complete desired sterilization including make-up charging of the chemically biocidal gas as required to maintain such biocidal gas concentration for an extended time period,
    determining unacceptable leakage of the chemically biocidal gas from the chamber by quantitatively monitoring such make-up charging of the chemically biocidal gas, and
    interrupting charging of chemically biocidal gas in response to such determination of unacceptable leakage.

2. The process of claim 1 in which maintaining biocidal gas concentration within the chamber includes
    sensing chamber pressure after establishing a desired pressure level above atmospheric pressure for the chemically biocidal gas in the chamber, and
    charging such biocidal gas under pressure when chamber pressure falls a predetermined increment below such established pressure level.

3. The process of claim 2 in which quantitatively monitoring make-up charging of the chemically biocidal gas comprises
    measuring time lapse between establishing such desired biocidal gas chamber pressure level and a predetermined pressure increment make-up charge of the chemically biocidal gas.

4. The process of claim 3 in which
    make-up charging of such biocidal gas is terminated when such time lapse falls below a predetermined value thereby indicating unacceptable leakage of such biocidal gas from said chamber.

5. The process of claim 1 in which quantitatively monitoring make-up charging of such biocidal gas comprises
    measuring decrease in concentration of the chemically biocidal gas in the chamber as an indication of unacceptable leakage of such biocidal gas from said chamber, and
    comparing such measurement with a predetermined standard.

6. The process of claims 1, 2, 3, or 5 further including the step of
    interrupting such sterilizing phase and exhausting the chemically biocidal gas from the chamber responsive to such determination which indicates unacceptable leakage of such biocidal gas from said chamber.

7. The process of claims 1, 2, 3, 4, or 5 in which such step of determining such unacceptable biocidal gas leakage from the sterilizing chamber further includes
    compensating for load absorption of the chemically biocidal gas by the goods to be sterilized.

8. The process of claims 2 or 3 further including the steps of
    compensating for load absorption of the chemically biocidal gas by
    providing a first make-up charge of such biocidal gas after establishing a desired biocidal gas pressure level in the sterilizing chamber, sugh first make-up charge providing for absorption of such biocidal gas by the goods to be sterilized, and
    measuring the interim between completion of such first make-up charge of such biocidal gas and a subsequent incremental decrease in sterilizing chamber pressure calling for make-up charging of such biocidal gas.

9. The process of claim 7 further including the steps of
    conditioning the goods to be sterilized by introducing a conditioning vapor into the chamber to heat and moisturize the goods, and
    evaluating load absorption characteristics during conditioning of the goods to be sterilized.

* * * * *